United States Patent [19]

Murdock

[11] 4,375,469

[45] Mar. 1, 1983

[54] OXAZA HETEROCYCLE-ANTHRAQUINONES, PHARMACEUTICAL COMPOSITIONS THEREOF AND METHOD OF USE THEREOF

[75] Inventor: Keith C. Murdock, Pearl River, N.Y.

[73] Assignee: American Cyanamid Company, Stamford, Conn.

[21] Appl. No.: 345,671

[22] Filed: Feb. 4, 1982

[51] Int. Cl.³ .................... A61K 31/55; C07D 273/06; A61K 31/535; C07D 265/32
[52] U.S. Cl. ............................... 424/244; 424/248.56; 260/239.3 T; 260/239.3 R; 544/79; 544/244
[58] Field of Search ........ 260/239 B, 239 T, 239.3 R; 544/79, 156; 424/244, 248.56

[56] References Cited

U.S. PATENT DOCUMENTS 3,646,072  2/1972  James .................................. 260/380
4,197,249  4/1980  Murdock ............................ 260/380

OTHER PUBLICATIONS

Murdock et al., J. Med. Chem., 22,1024, (1979).
Zee-Cheng et al., J. Med. Chem., 21,291, (1978).

Primary Examiner—Robert T. Bond
Attorney, Agent, or Firm—Mary-Ellen M. Timbers; Edward A. Conroy, Jr.

[57] ABSTRACT

Novel 1,4-di(substituted amino)-5,8-dihydroxyanthraquinones wherein the substituents are alkylamino alcohol and/or alkyl cyclicamide and their pharmacologically acceptable acid-addition salts useful as antitumor and chelating agents are described.

20 Claims, No Drawings

OXAZA HETEROCYCLE-ANTHRAQUINONES, PHARMACEUTICAL COMPOSITIONS THEREOF AND METHOD OF USE THEREOF

BACKGROUND OF THE INVENTION

The invention relates to 1,4-di[substituted amino]-5,8-dihydroxyanthraquinones wherein the substituents are alkylamino-alcohol and/or alkyl oxaza heterocycle groups. The compounds are antitumor agents active against leukemia and melanoma.

Research for antineoplastic agents for the suppression of malignant cell growth has been and remains an area of intense interest. Several agents have been developed which inhibit growth of cancerous tumors. These include such agents as methotrexate and 5-fluorouracil. Additional agents include those described in U.S. Pat. No. 4,197.249.

SUMMARY OF THE INVENTION

The present invention is directed to 1,4-di[substituted amino]-5,8-dihydroxyanthraquinones. These anthraquinone derivatives have generic formula I

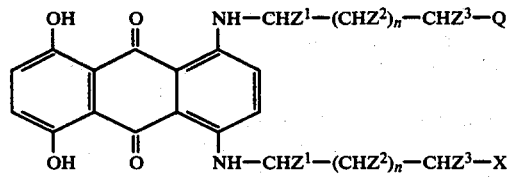

or a pharmacologically acceptable acid-addition salt thereof, wherein

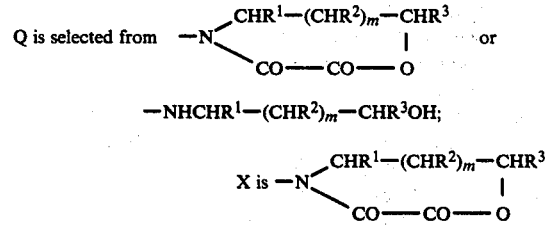

$R^1$, $R^2$ and $R^3$ are each independently selected from hydrogen or alkyl of 1 to 3 carbons; $Z^1$, $Z^2$ and $Z^3$ are each independently selected from alkyl of 1 to 2 carbons or hydrogen; n is 0 or 1; and m is 0 or 1.

The invention is directed as well to a pharmaceutical composition useful for controlling tumor growth and a method for inducing regression and/or palliation of leukemia cell growth or inhibiting growth of solid tumors, which employ an anthraquinone derivative of formula I. The pharmaceutical composition comprises an effective amount of a derivative in combination with a pharmaceutical carrier. The method for inducing regression or inhibition comprises administering by injection an effective amount of a derivative of formula I. For the composition and method, a preferred effective amount is about 3 mg to about 1.2 g per square meter of body surface area of the patient to be treated.

Preferred anthraquinone derivatives of formula I include those wherein $R^1$, $R^2$ and $R^3$ independently are hydrogen or alkyl of 1 to 2 carbons, those wherein $Z^1$, $Z^2$ and $Z^3$ are each hydrogen, those wherein n is 0, those wherein m is 0 and $R^1$ and $R^3$ are hydrogen and those wherein m is 0 and $R^1$ and $R^3$ are methyl or ethyl.

Especially preferred derivatives of formula I include those wherein:

(a) $Z^1$, $Z^2$ and $Z^3$ are H, Q and X are both

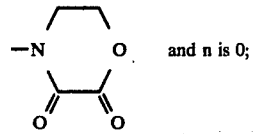 and n is 0;

(b) $Z^1$, $Z^2$ and $Z^3$ are H, Q is —NHCH$_2$CH$_2$OH, X is

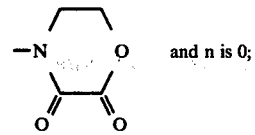 and n is 0;

(c) $Z^1$, $Z^2$ and $Z^3$ are H, Q and X are both

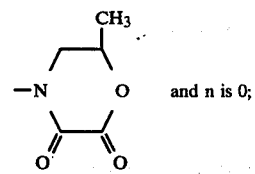 and n is 0;

(d) $Z^1$, $Z^2$ and $Z^3$ are H, Q is —NHCH$_2$—CH(CH$_3$)OH, X is

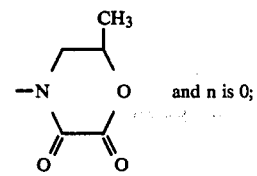 and n is 0;

(e) $Z^1$, $Z^2$ and $Z^3$ are H, Q and X are both

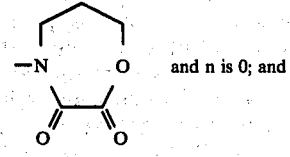 and n is 0; and (f) $Z^1$, $Z^2$ and $Z^3$ are H, Q is —NHCH$_2$CH$_2$CH$_2$OH, X is

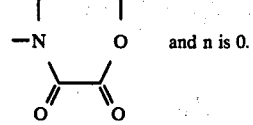 and n is 0.

DETAILED DESCRIPTION OF THE INVENTION

The anthraquinone derivatives of the present invention are blue-black crystalline solids which may be prepared by the following reaction scheme:

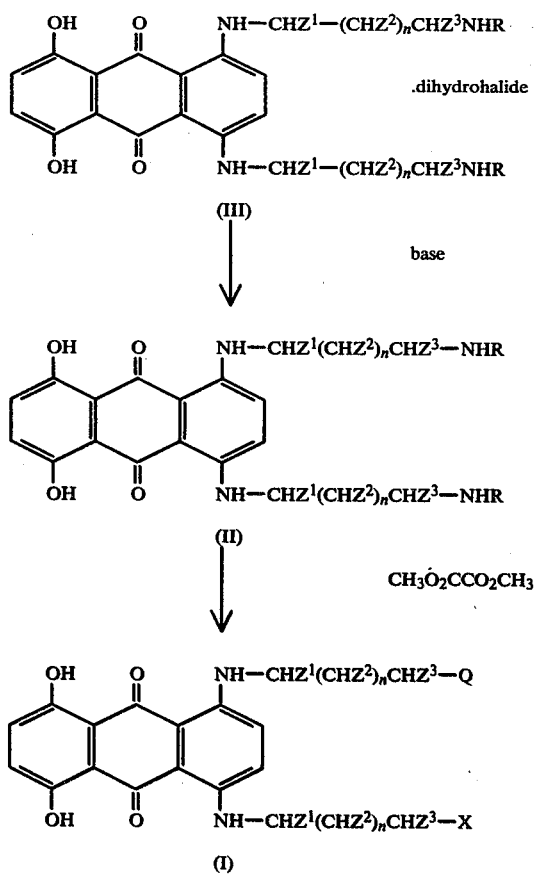

where

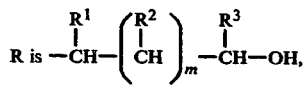

where m is 0 or 1 and $Z^1$, $Z^2$ and $Z^3$, $R^1$, $R^2$, $R^3$, Q, n and X are as defined above.

In accordance with the foregoing reaction scheme a 1,4-dihydroxy-5,8-bis[omega-(hydroxyalkylamino)alkylamino]anthraquinone dihydrohalide of formula III, the preparative method for which will be described infra, in a polar organic solvent such as methanol, ethanol, dimethylformamide and the like is cooled to at least below 20° C. such as in an ice bath and saturated with a nitrogen base such as ammonia, triethylamine or trimethylamine to yield the corresponding free base II. The free base may be converted to a doubly cyclized derivative of formula I, where Q and X are both $$-N \begin{matrix} R^1 \\ CH- \end{matrix} \left( \begin{matrix} R^2 \\ CH \end{matrix} \right)_m \begin{matrix} R^3 \\ -CH \\ \end{matrix} \begin{matrix} \\ O \\ \end{matrix} \\ \overset{|}{C} - \overset{|}{C} \\ \overset{\|}{O} \;\; \overset{\|}{O}$$

by reacting the free base with more than two equivalents of a dialkyl oxalate having 1 to 3 carbons in each alkyl group. The reaction is conducted in a polar, aprotic, inert organic solvent such as N,N-dimethylformamide or dimethylsulfoxide for about 18–96 hours, preferably 72 hours at a temperature of from ambient to 150° C. or reflux, preferably ambient temperature.

A derivative of formula I wherein Q is the linear hydroxyalkylamine moiety may be produced from the free base by reacting the free base with one equivalent of a dialkyl oxalate having 1 to 3 carbons in each alkyl group. The reaction is conducted in a polar, aprotic, inert, organic solvent such as dimethylsulfoxide or N,N-dimethylformamide at a temperature of from about ambient to reflux, preferably 120°–130° C., for ½ to 3 hours, preferably 1 hour. The derivative obtained is of formula I wherein

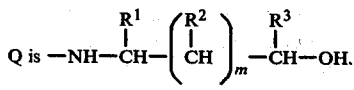

The derivatives produced by either of the two foregoing processes may be purified be recrystallization or by leaching with lower alkanols. Purity is established by analytical procedures such as elemental analysis as well as by thin layer chromatography studies of the absence of starting material.

Alternative methods for synthetic transformation of the free base of formula II to a doubly cyclized derivative of formula I or a derivative of formula I wherein Q is the linear moiety include reaction of the free base with appropriate amounts (more than 2 equivalents and 1 equivalent respectively) of dialkyl dithiooxalate or oxalyl chloride. Generally, the foregoing conditions employed for the dialkyl oxalate reactions can be used. Oxalyl chloride, however, requires addition of an acid scavenger such as pyridine or triethyl amine. The reaction of the free base with one equivalent of oxalyl chloride may preferably be conducted at as low a temperature as possible while maintaining the starting materials in solution in order to minimize possible intermolecular coupling and polymerization.

The starting anthraquinone dihydrohalide of formula III is prepared according to the methods described in U.S. Pat. No. 4,197,249, which is incorporated herein by reference. In general, leuco 1,4,5,8-tetrahydroxyanthraquinone is condensed with at least two equivalents of an N-(w-hydroxyalkyl)alkylene diamine of the formula $NH_2CHZ^1(CHZ^2)_nCHZ^3NHR$ wherein $Z^1$, $Z^2$, $Z^3$, R and n are defined as given supra, in a polar, protic or aprotic solvent such as alkanol, water, dimethylformamide, N,N,$N^1$,$N^1$-tetramethylethylenediamine or mixtures thereof. The condensation is typically conducted under a nitrogen atmosphere at a temperature of from about ambient to about 100° C., preferably 40°–60° C. for about 30 minutes to 24 hours, preferably 3–6 hours to produce a leuco base of formula A:

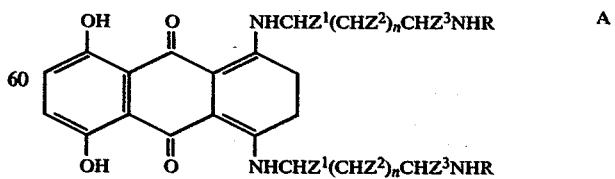

(R is $CHR^1(CHR^2)_mCHR^3OH$)

The leuco base of formula A is then converted to the aromatic free base of formula II by oxidative methods known to those skilled in the art. These methods include air oxidation by bubbling air through a solution of A, oxidation with hot nitrobenzene, oxidation in solution with about an equivalent of chloranil, hydrogen peroxide or sodium perborate. The dihydrohalide salt of formula III is prepared from the free base of formula II by adding about an equivalent or somewhat more of hydrogen halide to a solution of the free base in an alkanol solvent. The salt is precipitated by addition of a nonpolar solvent such as ester, chloroform and the like. Maintaining the starting material in the salt form is desirable since it can be readily repurified and has a crystalline character.

The novel derivatives of the present invention are antineoplastic agents which can inhibit the growth of transplanted mouse tumors in mice as established by the following tests.

Lymphocytic Leukemia P388 Test

The animals used were DBA/2 mice all of one sex, weighing a minimum of 17 g and all within a 3 g weight range. There were 5 or 6 animals per test group. The tumor transplant was accomplished by intraperitoneal injection of 0.5 ml of dilute ascitic fluid containing $10^6$ cells of lymphocytic leukemia P388. Various doses of the test derivatives, as indicated in Table 1, were administered intraperitoneally on days 1, 5 and 9 (relative to tumor inoculation). The animals were weighed and survivors were recorded on a regular basis for 30 days. The median survival time and the ratio of survival time for treated (T)/control (C) animals were calculated. The positive control compound was 5-fluorouracil given as a 60 mg/kg injection. The results of this test with an anthraquinone derivative of the present invention are summarized in Table I. The single positive control run established the validity of all derivative tests since they were all conducted under the same conditions on the same day. The criterion for efficacy is $T/C \times 100 \geq 125\%$.

balanced salt solution and a 0.5 ml aliquot of the homogenate was implanted intraperitoneally into each of the test mice. Various doses of the test derivative, as indicated in Table II, were administered intraperitoneally on days 1 through 9 (relative to tumor inoculation). The animals were weighed and survivors were recorded on a regular basis for 60 days. The median survival time and the ratio of survival time for treated (T)/control (C) animals were calculated. The positive control compound was 5-fluorouracil given as a 20 mg/kg injection. The results of this test with an anthraquinone derivative of the present invention are summarized in Table II. The single positive control run established the validity of all derivative tests since they were conducted under the same conditions on the same day. The criterion for efficacy is $T/C \times 100 \geq 125\%$.

TABLE II

Melanotic Melanoma B16 Test

| Compound | Dose (mg./kg.) | Median Survival Time (Days) | T/C × 100 (Percent) |
|---|---|---|---|
| 4,4'-[5,8-Dihydroxy-1,4-anthraquinonylenebis(iminoethylene)]-di-2,3-morpholinedione | 50 | 52.0 | 335 |
| | 25 | >54.0 | >348 |
| | 12.5 | 36.0 | 232 |
| | 6.2 | 36.5 | 235 |
| | 3.1 | 29.0 | 187 |
| | 1.5 | 23.0 | 148 |
| Control | — | 15.5 | — |
| 5-Fluorouracil | 20.0 | 25.0 | 161 |
| 1-[[2-(2,3-Dioxomorpholino)ethyl]amino]-5,8-dihyroxy-4-[[2-(2-hydroxyethylamino)ethyl]amino]-anthraquinone | 12.8 | >46.0 | >224 |
| | 3.2 | 34.5 | 168 |
| | 0.8 | 29.0 | 142 |
| | 0.2 | 26.0 | 127 |
| Control | — | 20.8 | — |

The novel derivatives of the present invention can inhibit tumor growth such as is produced in the transplanted mouse tumor test and can induce regression and/or palliation of leukemia and related cancers in

TABLE I

Lymphocytic Leukemia P388 Test

| Compound | Dose (mg./kg.) | Median Survival Time (Days) | T/C × 100 (Percent) | "Cures"* |
|---|---|---|---|---|
| 4,4'-[5,8-Dihydroxy-1,4-anthraquinonylenebis(iminoethylene)]-di-2,3-morpholinedione | 200 | >30.0 | >261 | 4/6 |
| | 100 | >30.0 | >261 | 3/6 |
| | 50 | >30.0 | >261 | 1/6 |
| | 50 | 23.5 | 204 | |
| | 12.5 | 21.0 | 183 | |
| | 6.25 | 21.0 | 183 | |
| | 3.12 | 24.0 | 209 | |
| | 1.56 | 18.5 | 161 | |
| | 0.78 | 17.0 | 148 | |
| Control | — | 11.5 | — | |
| 5-Fluorouracil | 60 | 19.0 | 165 | |
| 1-[[2-(2,3-Dioxomorpholino)ethyl]amino]-5,8-dihydroxy-4-[[2-(2-hydroxyethylamino)ethyl]amino]-anthraquinone | 200 | 20.5 | 220 | |
| | 50 | 20.0 | 215 | |
| | 12 | 19.0 | 204 | |
| | 6.4 | 17.5** | 170 | |
| | 3 | 15.0 | 161 | |
| | 1.6 | 18.0** | 175 | |
| | 0.8 | 14.0 | 151 | |
| | 0.4 | 15.5** | 150 | |
| | 0.1 | 13.0** | 126 | |
| Control | — | 9.3 | — | |

*"Cures" = number of survivors/total at 60 days.
**Median survival time for controls = 10.25 days.

Melanotic Melanoma B16

The animals used were C57BL/6 and BDF$_1$ mice, all of the same sex, weighing a minimum of 17 g and all within a 3 g weight range. There were normally 10 animals per test group. A one gram portion of melanotic melanoma B16 tumor was homogenized in 10 ml of cold patients when administered in amounts ranging from about 3 mg to about 1.2 g per square meter of body surface per day. [The interrelationship of dosages for animals of various sizes and species and humans (based on mg/m$^2$ of surface area) is described by Freireich, E.

J., et. al., Quantitative Comparison of Toxicity of Anticancer Agents in Mouse, Rat, Hamster, Dog, Monkey and Man. *Cancer Chemother Rep,* 50 No. 4, 219–244, (1966).] The course of treatment and dosage regimen for a patient will be determined by his unique condition and the judgment of his physician. In general, however, a typical dosage regimen for good results would be from about 3 mg to about 150 mg/m$^2$/day. The dosage units employed will total from about 5.4 mg to about 270 mg of the derivative for a subject of about 70 kg of body weight when administered over a 24 hour period. This dosage regimen would be adjusted according to the physician's judgment to provide a favorable therapeutic response. For example, several divided doses may be administered daily or the dose may be proportionally reduced as indicated by the exigencies of the therapeutic situation.

The derivatives may be administered parenterally, intramuscularly, subcutaneously, intravenously, or intraperitoneally. Solutions or dispersions of the active derivative as a free base or pharmaceutically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid so that syringe injection can be performed. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of micro-organisms can be brought about by various antibacterial and antifungal agents, for example, parabens, chlorobutanol, phenol, sorbic acid, thimerosal, and the like. In many cases it will be preferable to include isotonic agents, for example, sugars or sodium chloride. Prolonged absorption of the injectable compositions can be brought about by the use in the compositions of agents delaying absorption, for example aluminum monostearate and gelatin.

Sterile injectable solutions are prepared by incorporating the active derivative in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the other required ingredients from those enumerated above. In the case of sterile powders for the preparation of sterile injectable solutions, the preferred methods of preparation are vacuum drying and the freeze-drying techniques which yield a powder of the active derivative plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active derivative, its use in the pharmaceutical compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active derivative calculated to produce the desired pharmaceutical carrier. The specification for the novel dosage unit forms of the invention are dictated by and directly dependent on (a) the unique characteristics of the active derivative and the particular therapeutic effect to be achieved, and (b) the limitations inherent in the art of compounding such an active derivative for the treatment of disease in living subjects having a diseased condition in which bodily health is impaired as herein disclosed in detail.

The derivative is compounded for convenient and effective administration in effective amounts with a suitable pharmaceutically acceptable carrier in dosage unit form as hereinbefore disclosed. A unit dosage form can, for example, contain the principal active derivative in amounts ranging from about 0.1 to about 500 mg, with from about 10 to about 500 mg being preferred. Expressed in proportions, the active derivative is generally present in from about 10 to about 100 mg/ml of carrier. In the case of compositions containing supplementary active ingredients, the dosages are determined by reference to the usual dose and manner of administration of said ingredients.

Regression and palliation of cancers are attained, for example, using intreperitoneal administration. A single intravenous dosage or repeated daily dosages can be administered. Daily dosages of up to about 5 or 10 days are often sufficient. It is also possible to dispense one daily dosage or one dose on alternate or less frequent days. As can be seen from the dosage regimens, the amount of active derivative administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas and mammary tumors. By regression and palliation is meant arresting or retarding the growth of the tumor or other manifestation of the disease compared to the course of the disease in the absence of treatment.

The novel derivatives described herein are also useful as chelating, complexing or sequestering agents. The complexes formed with polyvalent metal ions are particularly stable. These properties render them useful for a variety of purposes wherein metal ion contamination presents a problem, e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by the materials and as metal carriers. Other uses common to sequestering agents are also apparent for these compounds.

The following examples are illustrative of the methods for preparing derivatives of the invention as well as pharmaceutical compositions thereof. They supplement the foregoing description of the invention and are not meant as limitations thereof.

EXAMPLE 1

4,4'-[5,8-Dihydroxy-1,4-anthraquinonylenebis(iminoethylene)]di-2,3-morpholinedione, Anthraquinone Derivative 100

(A) A mixture of 30.0 g of 1,4-bis[2-(2-hydroxyethylamino)ethylamino]-5,8-dihydroxyanthraquinone dihydrochloride (which was prepared according to the procedures in Examples 14 and 24 of U.S. Pat. No. 4,197,249) and 300 ml of methanol was chilled in an ice bath in a Dewar flask. The mixture was maintained at ice bath temperature while saturating it with ammonia. It was then allowed to stand at ice bath temperature for about 1 hour and anhydrous ammonia was allowed to flow continuously through it. The solid material in the mixture was collected by filtration and washed by slurrying with five 150 ml portions of methanol saturated with ammonia gas to yield 22.9 g of free base 101, 1,4-bis[2-(2-hydroxyethylamino)ethyl amino]-5,8-dihydroxyanthraquinone, as blue-black micro rods, m.p. 175°–178° C.

(B) A suspension of 3.11 g (7.0 mmol) of free base 101 in a solution of 35 ml of dry N,N-diemthylformamide and 5.90 (50 mmol) of dimethyl oxalate was stirred first at 10° C., then at 22° C. for a total of 70 hours. The resulting reaction mixture was diluted with 70 ml of ether and the solid residue was filtered. The residue was washed 4 times with ether to give 3.83 g of the above-identified anthraquinone derivative 100 as a blue-black solid, m.p. 260°–263° C. NMR in $d_6$-dimethylsulfoxide, significant peaks in $\delta$ppm from tetramethyl silane: 7.65, 7.18, 4.56, 3.73. IR as a KBr pellet, significant peaks: 5.68, 5.92 microns. Elemental Analysis: Cal'd for $C_{20}H_{24}N_4O_{10}\cdot H_2O$: C-54.73, H-4.59, N-9.82; found: C-54.43, H-4.73, N-10.26.

EXAMPLE 2

1-[2-(2,3-Dioxomorpholino)ethylamino]-5,8-dihydroxy-4-[2-(2-hydroxyethylamino)-ethylamino]anthraquinone, Anthraquinone Derivatives 200

(A) A solution of 2.455 g (5.5 mmol) of 1,4-bis[2-(2-hydroxyethylamino)ethylamino]-5,8-dihydroxyanthraquinone free base 101 (which was prepared according to Example 1) and 0.650 g (5.5 mmol) of dimethyl oxalate in 25 ml of dried dimethylsulfoxide was stirred and heated at about 120°–130° C. for one hour under dry conditions. The solution was allowed to stand for 16 hours and then 250 ml of methanol was added to precipitate a finely divided solid material. The mixture was centrifuged at 18,000 G. The supernatant liquid was decanted and the centrifuged solid was dispersed in 125 ml of methanol, recollected by filtration and washed 3 times with methanol to yield 1.503 g of the above-identified anthraquinone derivative 200, blue-black particles, m.p. 168°–178° C. NMR in $d_6$-dimethyl sulfoxide and deuterated trifluoroacetic acid, significant peaks in $\delta$ppm from tetramethyl silane: 7.16. IR as a KBr pellet, significant peaks: 5.68, 5.93 microns. Elemental Analysis: Cal'd for $C_{24}H_{26}N_4O_8\cdot H_2O$: C-55.87, H-5.46, N-10.85; found: C-55.81, H-5.35, N-10.68.

(B) The product of the Example may be converted to a monohydrochloride salt by suspending the free base in ethanol and adding an equivalent amount of an ethanolic hydrogen chloride solution.

EXAMPLE 3

4,4'-[5,8-Dihydroxy-1,4-anthraquinonylenebis(iminoethylene)]bis[6-methyl-2,3-morpholinedione], Anthraquinone Derivative 300

A mixture of 6.0 g (5.5 mmol) of 1,4-dihydroxy-5,8-bis[2-[(2-hydroxypropylamino)ethylamino]anthraquinone dihydrochloride (which was prepared according to the procedures in Example 32 of U.S. Pat. No. 4,197,249) and 60 ml of methanol may be treated with anhydrous ammonia according to the procedure of Example 1 to yield free base 301, 1,4-dihydroxy-5,8-bis[2-[(2-hydroxypropylamino)ethylamino]-anthraquinone.

A suspension of 3.31 g (7.0 mmol) of free base 301 in a solution of 35 ml of N,N-dimethylformamide and 5.90 g (50 mmol) of dimethyl oxalate may be reacted as described in Example 1 to yield the above-identified anthraquinone derivative 300.

In a similar fashion, the derivatives wherein X and Q are cyclic may be prepared by employing the procedures outlined in Example 1 and substituting the appropriate 1,4-bis[w-(hydroxyalkylamino)alkylamino]-5,8-dihydroxyanthraquinone dihydrohalide or C1 to C3 alkyl substituted forms thereof, as depicted by formula III, for starting material free base 101 of Example 1.

EXAMPLE 4

1-[2-(6-Methyl-2,3-dioxomorpholino)ethylamino]-5,8-dihydroxy-4-[2-(2-hydroxypropylamino)ethylamino]anthraquinone A solution of 2.60 g of 1,4-dihydroxy-5,8-bis-[2-(2-hydroxypropylamino)ethylamino]anthraquinone (prepared in Example 3) and 0.650 g of dimethyl oxalate in 25.0 ml of dried dimethyl sulfoxide is processed as described in Example 2 to give the desired product as a blue-black solid.

In a similar fashion, the derivatives wherein X is cyclic and Q is linear may be prepared by employing the procedures outlined in Example 2 and substituting the appropriate 1,4-bis[w-(hydroxyalkylamino)alkylamino]-5,8-dihydroxyanthraquinone free base or C1 to C3 alkyl substituted forms thereof as depicted by formula III, for starting material free base 101 of Example 2.

EXAMPLE 5

Preparation of Parenteral Suspension

In a solution of 700 ml of propylene glycol and 200 ml of water for injection is suspended 20.0 g of 4,4'-[5,8-dihydroxy-1,4-anthraquinonylenebis(iminoethylene)]di-2,3-morpholinedione(100) with stirring. After suspension is complete, the volume is made up to 1000 ml with water for injection. The formulation is sterilized, filled into 5.0 ml ampoules each containing 2.0 ml (representing 40 mg of drug) and sealed under nitrogen.

EXAMPLE 6

Preparation of Parenteral Solution

A 20.0 g amount of 1-[[2-(2,3-dioxomorpholino)-ethyl]amino]-5,8-dihydroxy-4-[[2-(2-hydroxyethylamino)-ethyl]amino]anthraquinone monohydrochloride[Derivative 200] is dissolved in 800 ml of water for injection previously sparged with nitrogen, then 9.0 g of sodium chloride is added and the resulting solution is diluted to 1000 ml with water for injection. The solution is sterilized by passing through a 0.22 micron sterilizing membrane, then is aseptically filled into 5.0 ml or 10.0 ampoules (representing 100 mg or 200 mg of drug) and sealed under nitrogen.

EXAMPLE 7

Preparation of Parenteral Solution (Lyophilized)

The membrane sterilized solution of Example 6 is filled into 5 or 10 ml vials. The material is lyophilized and the vials are stoppered and stealed. The product is reconstituted with a suitable diluent immediately prior to use.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed invention are considered to be within the purview and scope of this invention and the following claims.

What is claimed is:

1. An anthraquinone of the formula

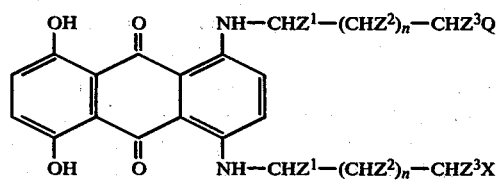

or a pharmaceutically acceptable acid-addition salt thereof, wherein:

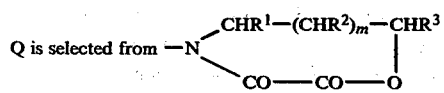

or $-NHCHR^1(CHR^2)_m CHR^3 OH$;

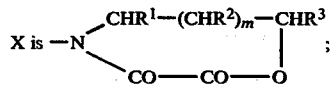

$R^1$, $R^2$ and $R^3$ are each independently selected from hydrogen or alkyl of 1 to 3 carbons; $Z^1$, $Z^2$ and $Z^3$ are each independently selected from hydrogen or alkyl of 1 to 2 carbons; and n is 0 or 1 and m is 0 or 1.

2. A pharmaceutical composition useful for inducing regression of leukemia cell growth or inhibiting growth of solid tumors in a patient, which comprises a pharmaceutical carrier in combination with an effective amount of an anthraquinone according to claim 1.

3. A method of inducing regression of leukemia cell growth in a patient or inhibiting growth of solid tumors in a patient, which comprises
administering by injection to said patient an effective amount of a compound according to claim 1.

4. A method according to claim 3 wherein the compound is in a pharmaceutical carrier.

5. A composition according to claim 2 wherein the effective amount is from about 3 mg to about 1.2 g per square meter of body surface area of the patient.

6. A method according to claim 3 wherein the effective amount is from about 3 mg to about 1.2 g per square meter of body surface area of the patient.

7. A composition according to claim 2 wherein the dosage amount of compound is from 0.1 mg to 500 mg per unit of formulated combination.

8. A compound according to claim 1, wherein $R^1$, $R^2$ and $R^3$ independently are hydrogen or alkyl of 1 to 2 carbons.

9. A compound according to claim 1, wherein m is 0, $R^1$ and $R^3$ are H.

10. A compound according to claim 1, wherein $Z^1$, $Z^2$ and $Z^3$ are each hydrogen.

11. A compound according to claim 1, wherein n is 0.

12. A compound according to claim 1, wherein m is 0, $R^1$ and $R^3$ independently are methyl or ethyl and $Z^1$, $Z^2$ and $Z^3$ are each hydrogen.

13. The compound according to claim 1, wherein $Z^1$, $Z^2$ and $Z^3$ are all hydrogen, Q and X are both

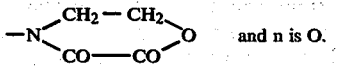

14. The compound according to claim 1, wherein $Z^1$, $Z^2$ and $Z^3$ are all hydrogen, Q is $-NHCH_2CH_2OH$, X is

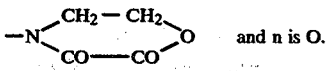

15. The compound according to claim 1, wherein $Z^1$, $Z^2$ and $Z^3$ are all hydrogen, Q and X are both

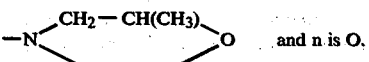

16. The compound according to claim 1, wherein $Z^1$, $Z^2$ and $Z^3$ are all hydrogen, Q is $-NHCH_2CH(CH_3)-OH$, X is

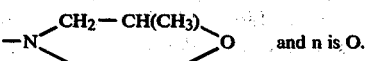

17. The compound according to claim 1, wherein $Z^1$, $Z^2$ and $Z^3$ are all hydrogen, Q and X are both

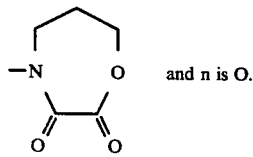 and n is 0.

18. The compound according to claim 1, wherein $Z^1$, $Z^2$ and $Z^3$ are all hydrogen, Q is -NHCH$_2$CH$_2$CH$_2$OH and X is

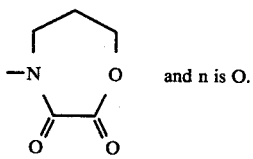 and n is 0.

19. A process for preparing a compound according to claim 1 wherein both Q and X are

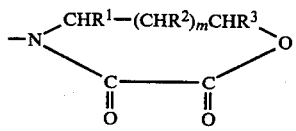

which comprises:

contacting a free base of formula II

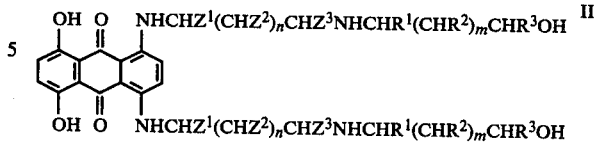

with at least two equivalents of dialkyl oxalate having 1 to 3 carbons in each alkyl group, in a polar, aprotic, inert, organic solvent at a temperature of from about 0° C. to solvent reflux temperature for about 18 to 96 hours.

20. A process for preparing a compound according to claim 1 wherein Q is NHCHR$^1$(CHR$^2$)$_m$CHR$^3$OH, which comprises:

contacting a free base of formula II

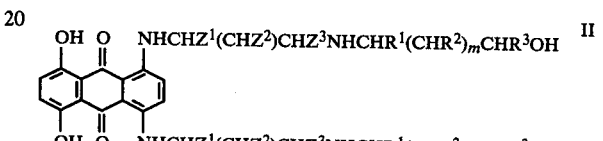

with one equivalent of dialkyl oxalate having 1 to 3 carbons in each alkyl group, in a polar, aprotic, inert, organic solvent at a temperature of from about ambient to about 130° C. for about 0.5 to 3 hours.

* * * * *